United States Patent
Frontera et al.

(10) Patent No.: US 9,484,179 B2
(45) Date of Patent: Nov. 1, 2016

(54) X-RAY TUBE WITH ADJUSTABLE INTENSITY PROFILE

(71) Applicant: General Electric Company, Schenectady, NY (US)

(72) Inventors: Mark Alan Frontera, Niskayuna, NY (US); Peter Andras Zavodszky, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 605 days.

(21) Appl. No.: 13/718,285

(22) Filed: Dec. 18, 2012

(65) Prior Publication Data
US 2014/0169523 A1    Jun. 19, 2014

(51) Int. Cl.
*H01J 35/14* (2006.01)
*H01J 35/06* (2006.01)
*H01J 35/04* (2006.01)
*A61B 6/03* (2006.01)

(52) U.S. Cl.
CPC .............. *H01J 35/14* (2013.01); *H01J 35/045* (2013.01); *H01J 35/06* (2013.01); *A61B 6/032* (2013.01)

(58) Field of Classification Search
None
See application file for complete search history.

(56) References Cited

U.S. PATENT DOCUMENTS

| | | | |
|---|---|---|---|
| 2,559,526 A | 7/1951 | Van De Graaf et al. | |
| 3,710,176 A | 1/1973 | Schlesinger | |
| 4,213,048 A | 7/1980 | Quang et al. | |
| 4,458,180 A | 7/1984 | Sohval et al. | |
| 4,631,742 A | 12/1986 | Oliver | |
| 4,912,367 A | 3/1990 | Schumacher et al. | |
| 5,199,054 A | 3/1993 | Adams et al. | |
| 5,332,945 A | 7/1994 | True | |
| 5,377,249 A * | 12/1994 | Wiesent ................. | A61B 6/032 378/10 |
| 5,438,605 A | 8/1995 | Burke et al. | |
| 5,617,464 A | 4/1997 | Mika et al. | |
| 5,812,632 A | 9/1998 | Schardt et al. | |
| 6,091,799 A | 7/2000 | Schmidt | |
| 6,094,009 A | 7/2000 | Goebel | |
| 6,570,165 B1 | 5/2003 | Engdahl et al. | |
| 6,652,143 B2 | 11/2003 | Popescu | |
| 6,785,359 B2 | 8/2004 | Lemaitre | |

(Continued)

FOREIGN PATENT DOCUMENTS

| | | |
|---|---|---|
| EP | 2 077 574 A1 | 7/2009 |
| JP | 2007051326 A | 3/2007 |

(Continued)

OTHER PUBLICATIONS

Jack et al.; "A Pulsed X-ray Generator"; (http://iopscience.iop.org/0022-3735/6/2/027); *J. Phys. E: Sci. Instrum.*; vol. 6; pp. 162-164; 1973.

*Primary Examiner* — Andrew Smyth
(74) *Attorney, Agent, or Firm* — Joseph F. Harding; The Small Patent Law Group, LLC

(57) ABSTRACT

An X-ray tube includes an emitter, and an electrode assembly. The emitter is configured to emit an electron beam toward a target. The electrode assembly includes at least one electrode having a bias voltage with respect to the emitter. At least one electrode of the electrode assembly is a segmented electrode including a plurality of segments. The plurality of segments includes a first member and a second member. The first member is configured to have a first bias voltage and the second member is configured to have a second bias voltage that is different from the first bias voltage.

20 Claims, 6 Drawing Sheets

(56) References Cited

U.S. PATENT DOCUMENTS

| | | | |
|---|---|---|---|
| 6,816,573 B2 | 11/2004 | Hirano et al. | |
| 6,912,268 B2 | 6/2005 | Price et al. | |
| 6,944,268 B2 | 9/2005 | Shimono | |
| 7,110,500 B2 | 9/2006 | Leek | |
| 7,545,901 B2* | 6/2009 | Mistretta | G06T 11/006 378/4 |
| 2001/0382163 | 11/2001 | Lee et al. | |
| 2002/0180364 A1 | 12/2002 | Ratzinger et al. | |
| 2003/0099327 A1 | 5/2003 | Matsushita et al. | |
| 2004/0240616 A1 | 12/2004 | Qiu et al. | |
| 2005/0105690 A1* | 5/2005 | Pau | G21K 7/00 378/145 |
| 2007/0009080 A1* | 1/2007 | Mistretta | G06T 11/006 378/4 |
| 2007/0053495 A1 | 3/2007 | Morton et al. | |
| 2008/0043920 A1 | 2/2008 | Liu et al. | |
| 2008/0067377 A1 | 3/2008 | Hatakeyama et al. | |
| 2008/0095317 A1 | 4/2008 | Lemaitre | |
| 2008/0187093 A1 | 8/2008 | Price et al. | |
| 2008/0260106 A1* | 10/2008 | Davilla | G06T 5/50 378/207 |
| 2010/0046712 A1 | 2/2010 | Behling | |
| 2010/0061516 A1 | 3/2010 | Freudenberger et al. | |
| 2010/0128846 A1 | 5/2010 | Balakin | |
| 2011/0038460 A1 | 2/2011 | Grasruck et al. | |
| 2011/0116593 A1 | 5/2011 | Zou et al. | |
| 2011/0142193 A1* | 6/2011 | Frontera | H01J 35/14 378/16 |
| 2012/0082292 A1* | 4/2012 | Zou | H01J 35/045 378/16 |
| 2014/0126704 A1* | 5/2014 | Zou | H01J 35/025 378/197 |

FOREIGN PATENT DOCUMENTS

| | | | | |
|---|---|---|---|---|
| JP | 2011129518 A | * | 6/2011 | |
| JP | 2012079695 A | * | 4/2012 | |
| WO | WO 0024030 A2 | * | 4/2000 | H01J 37/073 |
| WO | WO 0024030 A3 | * | 10/2002 | H01J 37/073 |
| WO | WO 2006/064403 A2 | | 6/2006 | |
| WO | WO 2007/135614 A1 | | 11/2007 | |
| WO | WO 2009/127995 A1 | | 10/2009 | |

* cited by examiner

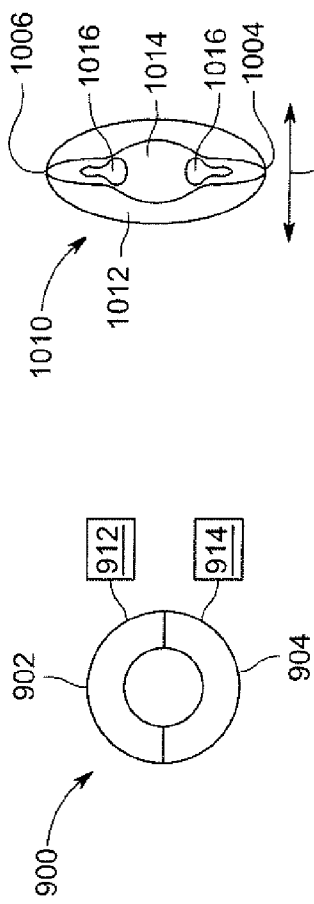
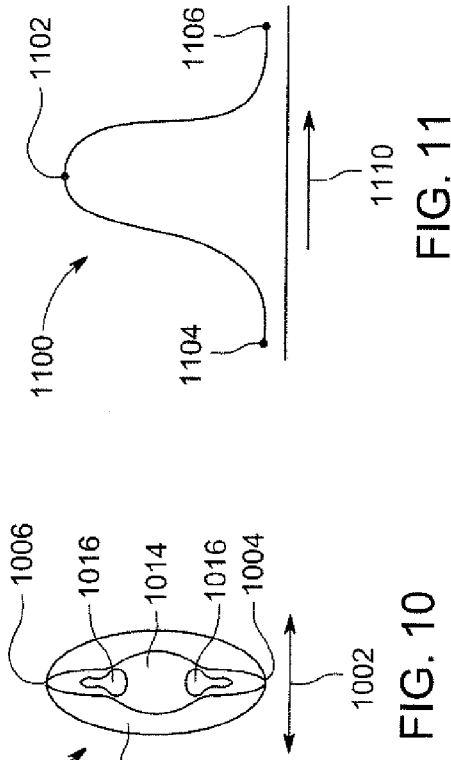
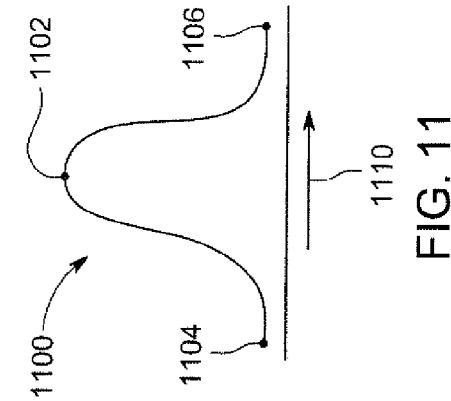
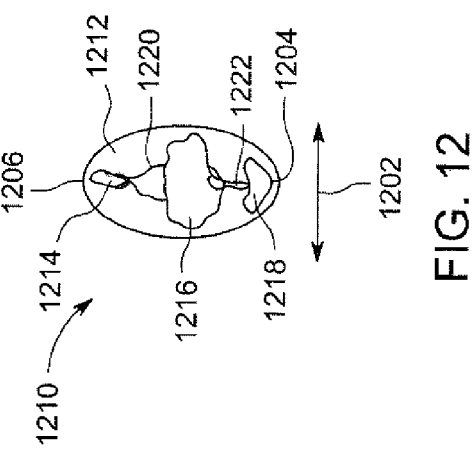
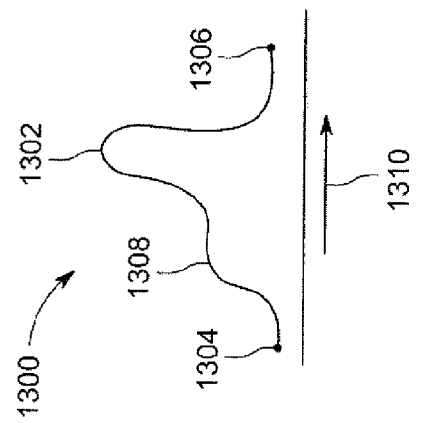

X-RAY TUBE WITH ADJUSTABLE INTENSITY PROFILE

BACKGROUND

X-ray tubes may be used in a variety of applications to scan objects and reconstruct one or more images of the object. For example, in computed tomography (CT) imaging systems an X-ray source emits a fan-shaped beam or a cone-shaped beam toward a subject or an object, such as a patient or a piece of luggage. The terms "subject" and "object" may be used to include anything that is capable of being imaged. The beam, after being attenuated by the subject, impinges upon an array of radiation detectors. The intensity of the attenuated beam radiation received at the detector array is typically dependent upon the attenuation of the X-ray beam by the subject. Each detector element of a detector array produces a separate electrical signal indicative of the attenuated beam received by each detector element. The electrical signals are transmitted to a data processing system for analysis. The data processing system processes the electrical signals to facilitate generation of an image.

Generally speaking, in CT systems, the X-ray source and the detector array are rotated about a gantry within an imaging plane and around the subject. Furthermore, the X-ray source generally includes an X-ray tube, which emits the X-ray beam at a focal point. Also, the X-ray detector or detector array in some systems includes a collimator for collimating X-ray beams received at the detector, a scintillator disposed adjacent to the collimator for converting X-rays to light energy, and photodiodes for receiving the light energy from the adjacent scintillator and producing electrical signals therefrom. In other systems, a direct conversion material, such as a semiconductor (e.g., Cadmium Zinc Telluride (CdZnTe)) may be used.

The X-ray tube, for example, may include an emitter from which an electron beam is emitted toward a target. The emitter may be configured as a cathode and the target as an anode, with the target at a substantially higher voltage than the emitter. Electrons from the emitter may be formed into a beam and directed or focused by electrodes and/or magnets. In response to the electron beam impinging the target, the target emits X-rays.

Uncontrolled variations in electron beam intensity and/or X-ray beam intensity may have a negative effect on image quality, for example due to artifacts or other issues, such as heel effect, hot-spots on an X-ray track, or the like. Further, a given beam profile for a conventional device is typically set during design or manufacture of the device, reducing the flexibility of the device to vary beam profile shaping from procedure to procedure or during a procedure for a given device.

BRIEF DESCRIPTION

In one embodiment, an X-ray tube assembly is provided. The X-ray tube assembly includes an emitter, an electrode assembly, and a control module. The emitter is configured to emit an electron beam defining a downstream direction toward a target. The emitter is disposed proximate an upstream end of the X-ray tube assembly. The electrode assembly is disposed proximate the emitter and downstream of the emitter, and includes at least one electrode having a bias voltage with respect to the emitter, with the electrode assembly configured to surround the electron beam in an axial direction. At least one electrode of the electrode assembly is a segmented electrode including a plurality of segments arranged about an axis defined by the electron beam. The plurality of segments includes a first member and a second member. The first member is configured to have a first bias voltage and the second member is configured to have a second bias voltage that is different from the first bias voltage.

In another embodiment, an X-ray tube assembly is provided. The X-ray tube assembly includes an emitter, a target, an electrode assembly, and a control module. The emitter is configured to emit an electron beam defining a downstream direction toward a target. The emitter is disposed proximate an upstream end of the X-ray tube assembly. The target is disposed proximate a downstream end of the X-ray tube assembly and configured to receive the electron beam emitted from the emitter. The target is configured to provide an X-ray beam responsive to a collision of the electron beam with the target. The electrode assembly is disposed proximate the emitter and downstream of the emitter, and includes at least one electrode having a bias voltage with respect to the emitter, with the electrode assembly configured to surround the electron beam in an axial direction. At least one electrode of the electrode assembly is a segmented electrode including a plurality of segments arranged about an axis defined by the electron beam. The plurality of segments includes a first member and a second member configured to have independently adjustable bias voltages. The control module is operably connected to the electrode assembly and configured to control a first bias voltage of the first member and a second bias voltage of the second member. A first beam intensity profile of a first beam directed toward a target is produced by a first combination of the first bias voltage and the second bias voltage, and a different, second beam intensity profile of a second beam directed toward the target from the emitter is produced by a different, second combination of the first bias voltage and the second bias voltage. The focusing magnet assembly is disposed downstream of the electrode assembly and upstream of the target, and is configured to deflect or position the electron beam on the target.

In a further embodiment, a method for providing an electron beam (e.g., an electron beam for X-ray generation) is provided. The method includes emitting an electron beam defining a downstream direction from an emitter toward a target. The method also includes focusing the electron beam using an electrode assembly having at least one electrode having a bias voltage with respect to the emitter. The electrode assembly includes at least one segmented electrode including a plurality of segments arranged about an axis defined by the electron beam. The plurality of segments includes a first member and a second member, with the first member and the second member configured to have independently adjustable bias voltages. The method also includes adjusting, via a control module, at least one of a first bias voltage of the first member and a second bias voltage of the second member from a first combination of bias voltages to a different, second combination of bias voltages. A first beam intensity profile of a first beam directed toward a target is produced by the first combination of the bias voltages, and a different, second beam intensity profile of a second beam directed toward the target from the emitter is produced by the second combination of the bias voltages.

BRIEF DESCRIPTION OF THE DRAWINGS

FIG. 9 is a schematic view of a segmented electrode in accordance with various embodiments.

FIG. 10 is an intensity profile for a focal spot in accordance with various embodiments.

FIG. 11 illustrates an intensity profile integrated across a width of the profile of FIG. 10 in accordance with various embodiments.

FIG. 12 is an intensity profile for a focal spot in accordance with various embodiments.

FIG. 13 illustrates an intensity profile integrated across a width of the profile of FIG. 12 in accordance with various embodiments.

DETAILED DESCRIPTION

Figure 1:
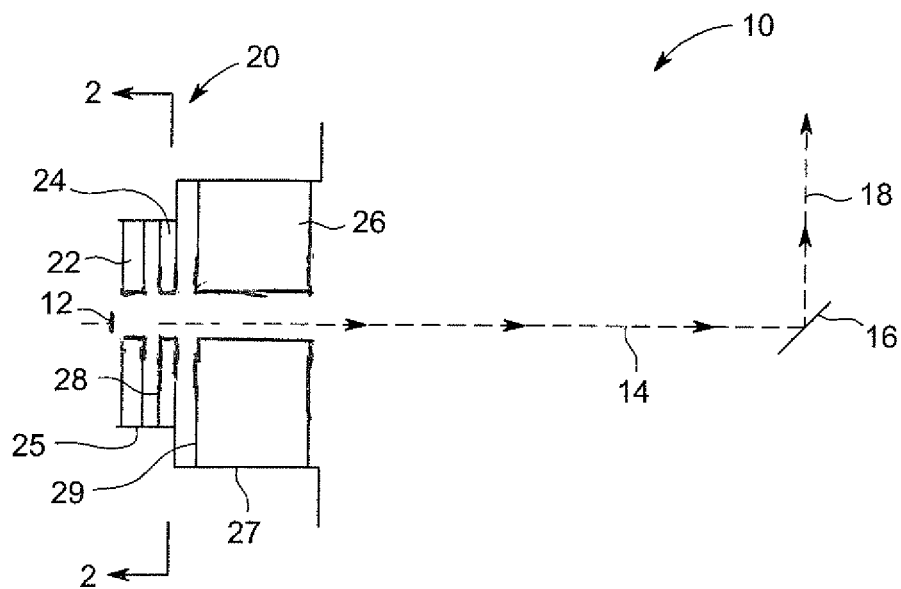
FIG. 1 is a schematic view of an X-ray tube assembly in accordance with various embodiments.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Systems formed in accordance with various embodiments provide an X-ray tube assembly having an electrode assembly positioned downstream (in the direction of electron beam travel) of an emitter. The electrode assembly is configured to focus and/or otherwise modify the electron beam as the electron beam travels downstream toward a target. One or more electrodes of the electrode assembly is split into segments disposed about an axis defined by the electron beam, with each segment receiving an independently set or adjustable bias voltage. Thus, the bias voltage of two or more segments may be varied with respect to each other, and allow for modification of an electron beam intensity profile and/or an electron beam shape. The electrode assembly may be operably connected to a controller that allows for dynamic adjustment of the electron beam intensity profile and/or shape during a procedure and/or between procedures.

A technical effect of at least one embodiment includes improved adjustability of electron beam intensity profiles and/or shapes. A technical effect of at least one embodiment includes providing dynamic adjustment capability for an electron beam intensity profile. A further technical effect of at least one embodiment is improved image quality and reduced image artifacts for X-ray imaging.

FIG. 1 is a schematic view of an X-ray tube assembly 10 formed in accordance with an embodiment. The X-ray tube assembly 10 includes an emitter 12 configured to emit an electron beam 14 toward a target 16. The X-ray tube assembly 10 also includes an electrode assembly 20 configured to focus or otherwise direct, shape, or influence the electron beam 14 as the electron beam proceeds in a downstream direction from the emitter 12 to the target 16. The target 16 emits an X-ray beam 18 responsive to the impingement of the electron beam 14 upon the target 16. The emitter 12 may be maintained at a negative voltage potential with respect to the target 16 so that electrons emitted from the emitter 12 flow toward the target 16.

In the illustrated embodiment, the electrode assembly 20 includes an emitter focusing electrode 22, an extraction electrode 24, and a downstream focusing electrode 26. In the illustrated embodiment, each of the emitter focusing electrode 22, extraction electrode 24, and downstream focusing electrode 26 are substantially cylindrical, or ring-shaped in cross-section, and configured to surround an axis defined by the electron beam 14 in an axial direction A depicted in FIG. 2. Returning to FIG. 1, the emitter focusing electrode 22 is disposed proximate the emitter 12 (in some embodiments the emitter focusing electrode 22 may overlap the emitter 12 in the downstream direction), the extraction electrode 24 is disposed downstream of the emitter 12 and the emitter focusing electrode 22, and the downstream focusing electrode 26 is disposed downstream of the extraction electrode 24. In various embodiments, one or more of the emitter focusing electrode 22, extraction electrode 24, and downstream focusing electrode 26 are provided with or maintained at a bias voltage with respect to the emitter 12 to control the shape or other feature of the electron beam 14 as the electron beam 14 progresses from the emitter 12 past the electrode assembly 20 in the downstream direction.

In the illustrated embodiment, the emitter focusing electrode 22 and the extraction electrode 24 are mounted to a first wall 25 of the X-ray tube assembly 10, and the downstream focusing electrode 26 is mounted to a second wall 27 of the X-ray tube assembly 10. In the illustrated embodiment, the depicted electrodes include substantially straight, or flat, bores. In some embodiments, one or more of the electrodes (or a portion thereof) may include a sloped bore, for example, such that the inner diameter of the electrode increases in the downstream direction. As shown in FIG. 1, the extraction electrode 24 and the downstream focusing electrode 26 of the illustrated embodiment include upstream walls 28, 29, respectively, that are substantially perpendicular to the axis defined by the electron beam 14. In some embodiments, the downstream focusing electrode 26 may be substantially larger in the downstream direction and/or in an axial direction than the extraction electrode 24, and/or may be configured to be maintained at a bias voltage having a substantially larger amplitude than a bias voltage of the extraction electrode. In various embodiments, other arrangements may be employed. For example, more or fewer numbers of electrodes may be employed, different mountings may be employed, and different geometries of electrodes may be employed. As another example, the upstream wall of one or more electrodes may be tapered or sloped with respect to the axis defined by the electron beam.

Figure 2:
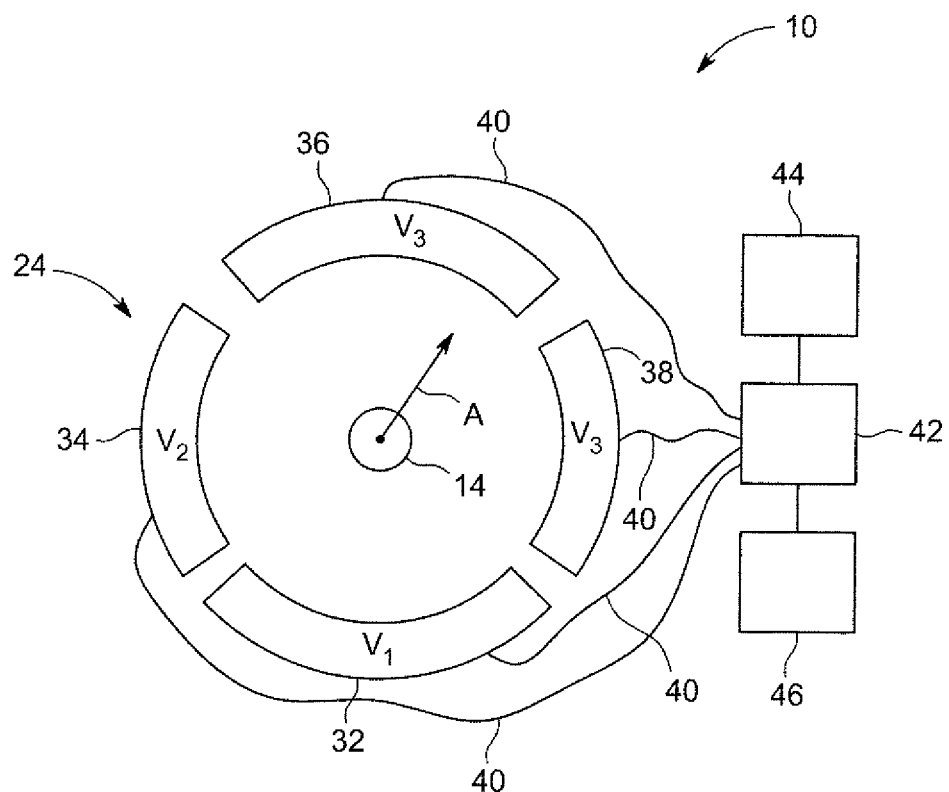
FIG. 2 is a sectional view through an electrode of the X-ray tube assembly of FIG. 1.

FIG. 2 is a sectional view through an electrode of the X-ray tube assembly 10 of FIG. 1. In the illustrated embodiment, FIG. 2 depicts a sectional view taken along line 2-2 through the extraction electrode 24 of FIG. 1. In the illustrated embodiment, the extraction electrode 24 is configured as a segmented electrode. The X-ray tube assembly 10 also includes a control module 42, a voltage source 44, and a user interface 46. The control module 42 controls the amount of voltage from the voltage source 44 provided to one or more portions of the electrode assembly 20 to control the electron beam 14. For example, the control module 42 may control a bias voltage (with respect to the emitter 12) of one or more portions of the electrode assembly 20 to control a beam intensity profile of the electron beam 14. In some embodiments, the control module 42 may control the voltages responsive to an input received from an operator via the user interface 46. In the illustrated embodiments, the control module 42 and voltage source 44 are depicted as single, integrated units. Other arrangements may be employed in various embodiments. In some embodiments, for example, one or more segments of the segmented extraction electrode 24 may have a separate, dedicated control module or submodule and/or voltage source associated therewith.

The extraction electrode 24 depicted in FIG. 2 includes four segments that define a ring around the electron beam path, or an axis defined by the electron beam 14. Each of the segments define a substantially circular arcuate segment corresponding to a quadrant of the ring defined by the extraction electrode 24. The ring defined by the extraction electrode 24 may be considered substantially continuous as the gaps between the individual segments are small compared to the segments, and the structure as a whole suggests a recognizable closed geometrical shape. In some embodiments, the gaps may be larger. In the illustrated embodiment, the segments from a ring or circle. In other embodiments, other shapes, such as ellipses, polygons, or the like may be formed by the segments. The segments are disposed so that a plane passing orthogonally through the segments (with the shape defined by the cross-section of the segments lying in the plane) is substantially perpendicular to the axis defined by the electron beam 14.

The extraction electrode 24 includes a first segment 32, a second segment 34, a third segment 36, and a fourth segment 38, with each segment corresponding to a quadrant of a ring defined by the extraction electrode 24. In the illustrated embodiment, the segments 32, 34, 36, and 38 are joined to the control module 42 via leads 40. The segments form opposed pairs, with each opposed pair being opposed to the other member of the pair symmetrically about the axis defined by the electron beam. In the illustrated embodiment, the first segment 32 and the third segment 36 form one opposed pair, and the second segment 34 and the fourth segment 38 form a second opposed pair.

The control module 42 is operably connected to the extraction electrode 24, the voltage source 44, and the user interface 46. The control module 42 is configured to control the voltage from the voltage source 44 provided to each segment 32, 34, 36, 38 so that each segment may be maintained at a given bias voltage relative to the emitter 12 independently from the other segments, and so that each segment may have a bias voltage associated therewith adjusted independently of the other segments. For example, in the illustrated embodiment, the first segment 32 has a bias voltage of V1, the second segment 34 has a bias voltage of V2, the third segment 36 has a bias voltage of V3, and the fourth segment 38 has a bias voltage of V4. In alternate embodiments, a common voltage (or current) source may provide voltage (or current) to various segments, with the segments passively biased with respect to each other. For example, each segment may be biased differently from at least one neighboring segment via the placement of a resistive bridge or fixed resistance differential between neighboring segments.

The user interface 46 is configured to allow an operator or practitioner to provide an input to change or alter one or more voltages provided to the electrode assembly 20 to control the beam intensity profile of the electron beam 14. For example, one or more of the various voltages provided to the segments 32, 34, 36, 38 may be adjusted to alter a beam intensity profile. In some embodiments, if an artifact is present, the beam intensity profile may be altered to address the artifact. As another example, if a heel effect (a gradient in X-ray intensities in the beam that may be caused by angling of the anode (e.g., the target)) is noted to be present, the beam intensity profile may be adjusted to address the heel effect. A beam intensity profile may be adjusted to compensate for hardening of a spectrum (e.g., the blocking of softer X-rays causing distortion as a result of a heel effect). For example, the beam intensity profile may be adjusted to provide increased intensity to a region or area that is being blocked or reduced by hardening or other heel effect. As one more example, the beam intensity profile may be altered to provide a desired profile for a given procedure, and subsequently altered to provide a different desired profile for a subsequent procedure. Thus, in some embodiments, a beam intensity profile may be adjusted to counteract a source of distortion (e.g., heel effect) by providing more electrons or intensity to a portion of a beam being blocked or inhibited. Further, in some embodiments, a beam intensity profile may be adjusted to shape the focal spot, for example to improve resolution or alter thermal loading. The user interface 46 may include a display screen, keyboard, mouse, touchscreen or the like. In some embodiments, the voltages may be controlled autonomously, for example by a control module.

In some embodiments, the user may specify the voltages for one or more electrode segments directly or indirectly. In various embodiments, the user may specify a desired electron beam intensity profile, desired X-ray focal spot intensity profile, and/or characteristic of the electron beam intensity profile or X-ray focal spot intensity profile, and a processing unit (e.g., the control module 42) may determine a corresponding voltage combination for the various electrode segments to achieve the desired profile or profile characteristic. In some embodiments, the user may specify a given procedure or application, and a processing unit (e.g., the control module 42) may determine a corresponding voltage combination for the various electrode segments to achieve the given procedure or application. The voltage combination, for example, may be pre-determined for different procedures, with the configurations correlated to corresponding procedures and tabulated in a database accessible by the processing unit. In some embodiments, a processing unit (e.g., the control module 42) may be configured to perform a diagnostic analysis (or receive such an analysis) of the electron beam, X-ray beam, and/or an image reconstructed using the X-ray beam, and to autonomously adjust one or more of the segment voltages to address an artifact or issue identified via the diagnostic analysis.

In some embodiments, one or more of the segment voltages may be a negative bias voltage with respect to the emitter, and the downstream focusing electrode 26 may have a positive voltage bias with respect to the emitter, such that one or more portions of an emitter surface of the emitter 12 are suppressed from emitting electrons, such that both, a shape and an intensity profile of the electron beam 12 may be adjusted or controlled. In some embodiments, all of the segment voltages may be negatively biased with respect to the emitter.

The above discussed arrangement of electrodes is meant by way of illustration and is not meant to be limiting. For example, in some embodiments, the downstream focusing electrode may be segmented while the extraction electrode is not segmented. As another example, in some embodiments, both the downstream focusing electrode and the extraction electrode may be segmented. In still other embodiments, other numbers or combinations of electrodes may be used. As one example, in some embodiments, an extraction electrode may be segmented, with at least one of the extraction electrodes having a positive voltage bias, and a downstream electrode may not be present.

Figure 3:
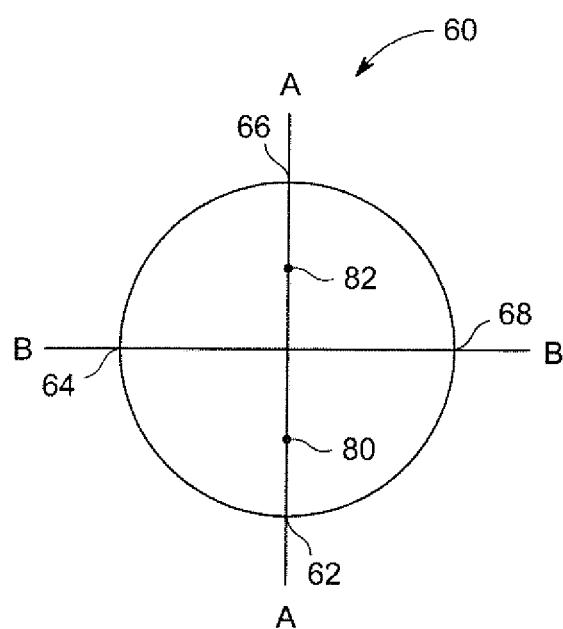
FIG. 3 is a view of an electron beam in accordance with various embodiments.

FIG. 3 is a view of beam profile 60 corresponding to the segmented electrode arrangement of FIG. 2. As the X-ray beam is produced by the collision of the electron beam against the target, the profile of the electron beam and the profile of the X-ray beam may correspond with each other. Further, by controlling or altering an electron beam profile, a corresponding control or alteration of the resulting X-ray beam may also by controlled. Thus, in connection with FIGS. 3 and 4, the beam profile 60 may be understood as corresponding to an electron beam profile or an X-ray beam profile (e.g., an X-ray focal spot profile). The beam profile 60 includes a first portion 62 (corresponding to the first segment 32 of the extraction electrode 24), a second portion 64 (corresponding to the second segment 34), a third portion 66 (corresponding to the third segment 36), and a fourth portion 68 corresponding to the fourth segment 38). The profile 60 is depicted on a set of axis including an axis AA corresponding to an axis through the centers of the first segment 32 and the third segment 36, and an axis BB corresponding to an axis through the centers of the second segment 34 and the fourth segment 38.

The beam profile 60 may have a varying intensity throughout a cross-sectional area. For clarity and ease of explanation, only variation along the axis AA will now be discussed. The general principles discussed apply to other variations (e.g., along axis BB).

Figure 4:
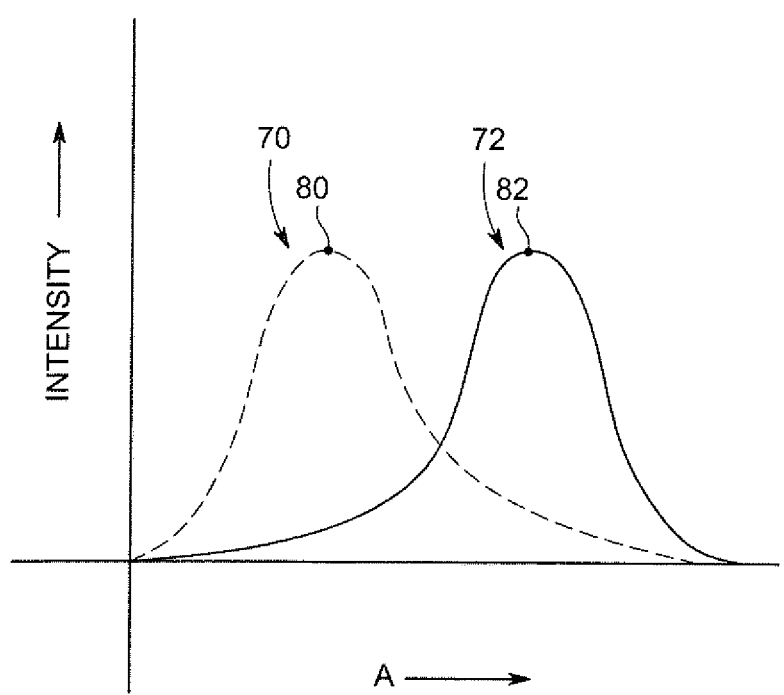
FIG. 4 is a graph of electron beam intensity along an axis in accordance with various embodiments.

FIG. 4 is a graph of electron beam intensity along the axis AA in accordance with various embodiments. Two electron beam intensity distributions along the length of axis AA are depicted in FIG. 4, namely an initial distribution 70, and a modified distribution 72. The initial distribution 70 has an initial peak 80, and the modified distribution 72 has a modified peak 82.

In an example scenario, the initial distribution 70 corresponds to voltage settings of V1=V2=V3=V4=$V_{initial}$, where $V_{initial}$ is an initial voltage at which all of the segments 32, 34, 36, 38 are set (see FIG. 3), with $V_{initial}$ at a positive bias relative to the emitter. (In alternate embodiments, one or more of the voltages may be at a negative bias voltage.) The resulting initial distribution 70 has an initial peak 80 shown in FIGS. 3 and 4, with the initial peak 80 shown in FIG. 4 as being closer to the first portion 62 of the beam profile 60, which corresponds to the first portion 32 of the extraction electrode 24. The initial peak 80 is depicted as lying substantially along the AA axis. In a given circumstance, it may be desirable to alter the beam profile 60 so that the intensity of the beam profile is described by the modified distribution 72 (e.g., with the peak intensity adjusted toward the third portion 66 of the beam profile 60).

The beam intensity may be adjusted by altering the bias voltages of the electrode segments. For example, with the peak desired to be moved from a point of the profile corresponding to the first segment 32 toward a point of the profile corresponding to the third segment 36, the relative voltages of the first segment 32 and the third segment 36 may be adjusted so that more electrons of the electron beam are drawn to the portion of the profile corresponding to the third segment 36 (e.g., third portion 66). For example, a positive voltage bias of the third segment 36 may be increased, and/or a positive voltage bias of the first segment 32 may be decreased. In the illustrated embodiments, the voltage V1 of the first segment 32 is reduced, the voltage V3 of the third segment 36 is increased, and the voltages V2 and V4 are maintained at $V_{initial}$ (with the peak remaining substantially along the axis AA). Additionally, the relative voltages of the second segment 34 and the fourth segment 38 may be altered to move a peak or adjust an intensity profile in a direction corresponding to the BB axis.

In the illustrated embodiment, the increasing of V3 and decreasing of V1 results in the modified peak 82 being biased toward the portion 66 of the profile 60 corresponding to the third segment 36, as shown in FIGS. 3 and 4. Providing a greater relative voltage change may move the modified peak 82 and distribution 72 more to the right in the sense of FIG. 4 (or upward in the sense of FIG. 3), while providing a lower relative voltage change may move the modified peak 82 less to the right of the initial peak 80 in the sense of FIG. 4.

FIGS. 9-13 provide additional examples of adjustment of beam intensity profiles or distributions. FIG. 9 provides a schematic view of a segmented electrode 900 formed in accordance with various embodiments. The segmented electrode 900 includes a first electrode segment 902 and a second electrode segment 904. The first electrode segment 902 is maintained at a first potential or first voltage 912, and the second electrode segment 904 is maintained at a second potential or second voltage 914. In the illustrated embodiment, the first electrode segment 902 and the second electrode segment have independently adjustable bias voltages. Thus, for example, the first and second voltages 912, 914 may be substantially the same at some instances in time, and different at other instances in time.

FIG. 10 illustrates an intensity profile 1010 for a focal spot produced using the segmented electrode 900 when the first voltage 912 and the second voltage 914 are positive and substantially the same. As can be seen in FIG. 10, such an intensity profile is generally symmetric. The intensity profile 1010 represents the distribution of electron density across a focal spot formed on a target by an electron beam passing through the segmented electrode 900. The intensity profile 1010 includes a first point 1004 corresponding to an edge of the focal spot corresponding to a point on the electron beam closest to the midpoint of the second electrode segment 904, and second point 1006 corresponding to an edge of the focal spot corresponding to a point on the electron beam closest to the midpoint of the first electrode segment 902. The intensity profile 1010 and the focal spot also define a width 1002 that reaches a maximum at a point about halfway between the first point 1004 and the second point 1006.

In the embodiment depicted in FIG. 10, the first and second voltages 912, 914 are substantially the same, resulting in a substantially symmetric intensity profile. The intensity profile 1010 includes a low intensity region 1012, a medium intensity region 1014, and two high intensity regions 1016. The two high intensity regions 1016 are substantially the same size and shape, and are located symmetrically about a horizontal (in the sense of FIG. 10) axis bisecting the intensity profile 1010.

FIG. 11 illustrates an intensity profile 1100 integrated across the width 1002 taken along a length 1110 bounded by the first point 1004 and the second point 1006. Thus, point 1104 corresponds to the intensity integrated across the width 1002 at the first point 1004, and point 1106 corresponds to the integrated intensity across the width 1002 at the second point 1006. The integrated intensity is generally at a minimum at the two points 1004 and 1006, as these are locations of both generally low intensity and minimum width 1002 as seen in FIG. 10. The integrated intensity 1100 of FIG. 11 reaches a peak at 1102, which corresponds generally to the horizontal midpoint (in the sense of FIG. 10) of the intensity profile 1010. While the high intensity regions 1016 are not located at this portion of the intensity profile 1010, the increased width 1002 at the midpoint may provide a higher sum of localized intensities across the greater width at the midpoint. That is, while the local intensity at any given point is highest within the high intensity regions 1016, the intensity integrated across the width of the profile (e.g., the sum of intensities along a width) may be greater at portions of the intensity profile 1010 having lower local intensities but a greater width across which to integrate or sum intensities.

FIG. 12 illustrates an intensity profile 1210 for a focal spot produced using the segmented electrode 900 when the first voltage 912 is greater than (e.g., more positive) the second voltage 914. As can be seen in FIG. 12, such an intensity profile is asymmetric. The intensity profile 1210 represents the distribution of electron density across a focal spot formed on a target by an electron beam passing through the segmented electrode 900. The intensity profile 1210 includes a first point 1204 corresponding to an edge of the focal spot corresponding to a point on the electron beam closest to the midpoint of the second electrode segment 904, and second point 1206 corresponding to an edge of the focal spot corresponding to a point on the electron beam closest to the midpoint of the first electrode segment 902. The intensity profile 1210 and the focal spot also define a width 1202 that reaches a maximum at a point about halfway between the first point 1204 and the second point 1206.

In the embodiment depicted in FIG. 12, the first and second voltages 912, 914 are different (the first voltage 912 is greater than the second voltage 914), resulting in an asymmetric intensity profile. The intensity profile 1210 includes a low intensity region 1212, medium intensity regions 1214, 1216, 1218 and two high intensity regions 1220 and 1222. The high intensity region 1222 is larger and wider than the high intensity region 1220. Generally speaking, the intensity of the profile 1210 is shifted toward the second point 1206 (corresponding to the midpoint of the first electrode 902), as the first voltage 912 of the first segment 902 is higher (more positive) than the second voltage 914 of the second segment 904.

FIG. 13 illustrates an intensity profile 1300 integrated across the width 1202 taken along a length 1310 bounded by the first point 1204 and the second point 1206. Thus, point 1304 corresponds to the intensity integrated across the width 1202 at the first point 1204, and point 1306 corresponds to the integrated intensity across the width 1202 at the second point 1206. The integrated intensity is generally at a minimum at the two points 1304 and 1306, as these are locations of both generally low intensity and minimum width 1202 as seen in FIG. 12. The integrated intensity 1300 of FIG. 13 reaches a first peak at 1308, which corresponds generally to a region proximate the juncture of the high intensity region 1222 and the medium intensity region 1216. The integrated intensity 1300 remains generally level for a distance as the length of the intensity profile 1210 is traversed away from the point 1204 and toward the point 1206, eventually increasing to a second peak 1302 that represents the maximum integrated intensity level. The second peak 1302 generally corresponds to a width that traverses a central portion of the high intensity region 1220 (the high intensity region 1220 is larger than the first high intensity region 1222). The integrated intensity than decreases toward a generally minimum level at or near point 1306 (which corresponds to point 1206).

It should be noted that the above examples of intensities and profiles are intended by way of example and not limitation. In other embodiments, other shapes of focal spots and/or intensity profiles may be achieved by adjusting, for example, the number and/or orientation of electrode segments, and/or the voltages associated with one or more electrode segments.

In some embodiments, the voltages of electrode segments may be dynamically controlled, and thus the intensity of the beam profile also dynamically controlled, for example, responsive to an analysis of a beam or image and/or operator input. An intensity profile may be adjusted to address a heel effect, address one or more artifacts, and/or allow different focal spots tailored for different procedures or applications. One or more segmented electrodes as discussed above may be used in connection with an X-ray tube assembly in accordance with embodiments as discussed below in connection with FIGS. 5-7.

Figure 5:
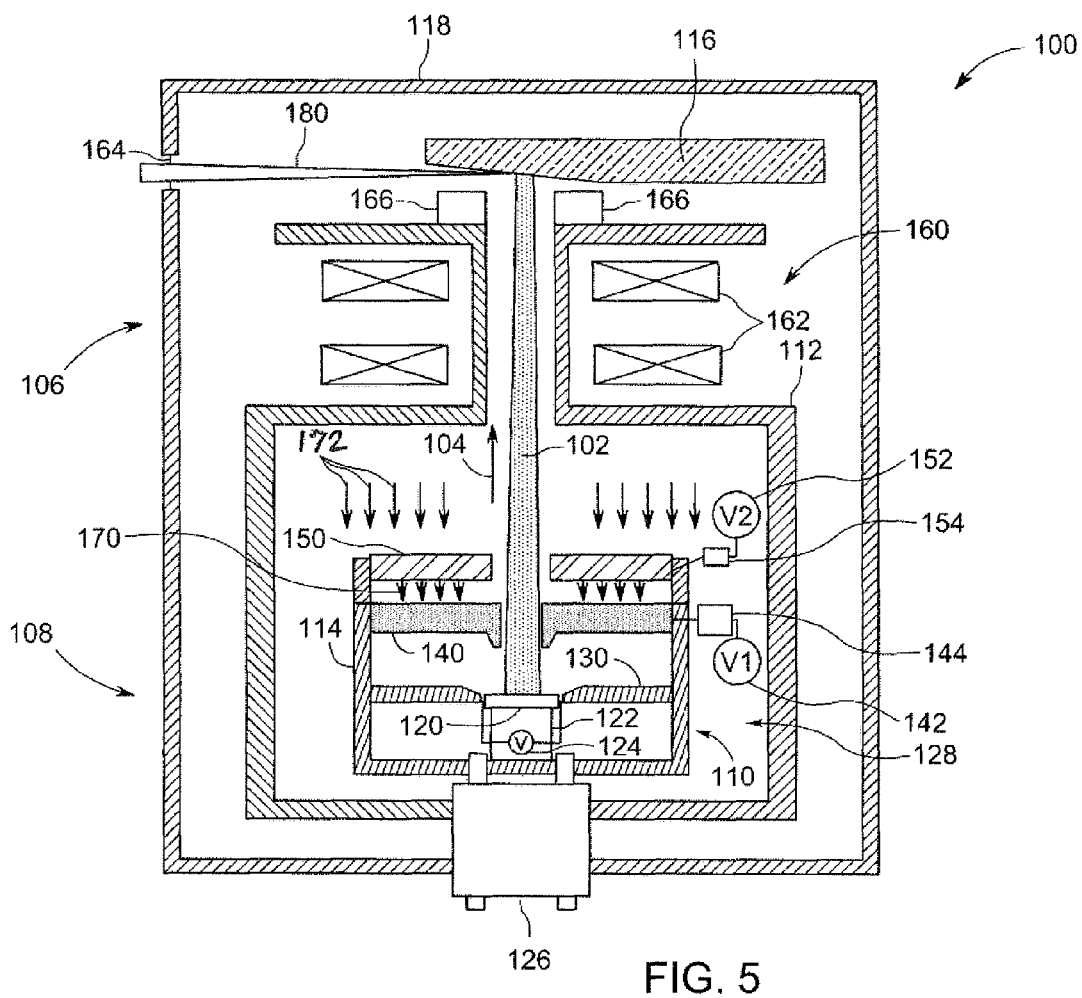
FIG. 5 is a sectional view of an X-ray tube assembly in accordance with various embodiments.

FIG. 5 is a sectional view of an X-ray tube assembly 100 formed in accordance with various embodiments. The X-ray tube assembly 100 includes an injector 110 disposed within a vacuum wall 112. The injector 110 may further include an injector wall 114 that encloses various components of the injector 110. In addition, the X-ray tube assembly 100 may also include an anode or target 116. The anode 116 is typically an X-ray target. The injector 110 and the target 116 are disposed within a tube casing 118. In some embodiments, the injector 110 may include at least one cathode in the form of an emitter 120. In various embodiments, the injector 110 may include a Pierce-type cathode. The cathode (e.g., emitter 120) may be directly heated in some embodiments, and indirectly heated in some embodiments. In the illustrated embodiments, the emitter 120 is coupled to an emitter support 122, with the emitter support 122 in turn coupled to the injector wall 114. The emitter 120 may be heated, for example, by passing a relatively large current through the emitter 120. A voltage source 124 may supply this current to the emitter 120. In some embodiments, a current of about 10 amps may be passed through the emitter 120. The emitter 120 may emit an electron beam 102 as a result of being heated by the current supplied by the voltage source 124. As used herein, the term "electron beam" may be used to refer to as a stream of electrons that have substantially similar velocities. The electron beam 102 defines a downstream direction 104 as the direction from the emitter 120 to the target 116. The X-ray assembly 100 includes a downstream end 106 and an upstream end 108, with the emitter 120 disposed proximate the upstream end 108 and the target 116 disposed proximate the downstream end 106. The electron beam 102 may a substantially uniform width, diameter, or cross-section along one or more portions of the length of the electron beam 102. In practice, other profiles may be employed. For example, the electron beam 102 may have a relatively small, substantially continuous taper along the length of the electron beam 102. As another example, the electron beam 102 may be tapered at different rates along different portions of the length of the electron beam.

The electron beam 102 may be directed towards the target 116 to produce X-rays 180. More particularly, the electron beam 102 may be accelerated from the emitter 120 towards the target 116 by applying a potential difference between the emitter 120 and the target 116. In some embodiments, a high voltage in a range from about 40 kiloVolts (kV) to about 450 kV may be applied via use of a high voltage feedthrough 126 to set up a potential difference between the emitter 120 and the target 116, thereby generating a high voltage main electric field 172 to accelerate the electrons in the electron beam 102 towards the target 116. In some embodiments, a high voltage potential difference of about 140 kV may be applied between the emitter 120 and the target 116. It may be noted that in some embodiments, the target 116 may be at ground potential. For example, in some embodiments, the emitter 120 may be at a potential of about −140 kV and the target 116 may be at ground potential or about zero volts.

In alternative embodiments, the emitter 120 may be maintained at ground potential and the target 116 may be maintained at a positive potential with respect to the emitter 120. By way of example, the target 116 may be at a potential of about 140 kV and the emitter 120 may be at ground potential or about zero volts. In some embodiments, a bi-polar target and emitter arrangement may be employed. For example, the emitter 120 may be maintained at a negative potential, the target 116 may be maintained at a positive potential, and a frame to which the emitter 120 and target 116 are secured may be grounded.

When the electron beam 102 impinges upon the target 116, a large amount of heat may be generated in the target 116. The heat generated in the target 116 may be significant enough to melt the target 116. In some embodiments, a rotating target may be used to address the problem of heat generation the target 116. For example, in some embodiments, the target 116 may be configured to rotate such that the electron beam 102 striking the target 116 does not cause the target 116 to melt since the electron beam 102 does not strike the target 116 substantially continuously at the same location. In some embodiments, the target 116 may include a stationary target. The target 116 may be made of a material that is capable of withstanding the heat generated by the impact of the electron beam 102. For example, the target 116 may include materials such as, but not limited to, tungsten, molybdenum, or copper.

In the illustrated embodiment, the emitter 120 is a flat emitter. In alternative configurations the emitter 120 may be a curved emitter. The curved emitter, which is typically concave in curvature, provides pre-focusing of the electron beam. As used herein, the term "curved emitter" may be used to refer to an emitter that has a curved emission surface. Further, the term "flat emitter" may be used to refer to an emitter that has a flat emission surface. It may be noted that emitters of different shapes or sizes may be employed based on particular requirements for a given application.

In some embodiments, the emitter 120 may be formed from a low work-function material. More particularly, the emitter 120 may be formed from a material that has a high melting point and is capable of stable electron emission at high temperatures. The low work-function material may include materials such as, but not limited to, tungsten, thoriated tungsten, lanthanum hexaboride, hafnium carbide, or the like. In some embodiments, the emitter 120 may be provided with a coating of a low work-function material.

With continuing reference to FIG. 5, the injector 110 of the illustrated embodiments includes an electrode assembly 128 including an emitter focusing electrode 130, an extraction electrode 140, and a downstream focusing electrode 150. One or more of the emitter focusing electrode 130, extraction electrode 140, or downstream focusing electrode 150 may be configured as a segmented electrode as discussed above. In the illustrated embodiment, the emitter focusing electrode 130 is disposed proximate the emitter 120, the extraction electrode 140 is disposed downstream of the emitter focusing electrode 130 and the emitter 120, and the downstream focusing electrode 150 is disposed downstream of the extraction electrode 140, with the extraction electrode 140 thus interposed between the emitter focusing electrode 130 and the downstream focusing electrode 150. The electrode assembly 128, or portions thereof, may be mounted to and/or enclosed by the injector wall 114. The particular geometries or arrangements of electrodes depicted in FIG. 5 are provided by way of example for simplicity and clarity of illustration and may differ in various embodiments. For example, one or more of the electrodes (e.g., the downstream focusing electrode) may have a larger outer diameter than other electrodes (e.g., the emitter focusing electrode and/or extraction electrode) and/or be mounted to an alternative wall or structure than injector wall 114. Also, one or more of the electrodes (e.g., the downstream focusing electrode) may have a greater length along an axis defined by the electron beam than other electrodes (e.g., the emitter focusing electrode and/or extraction electrode). Further, one or more of the electrodes may have a tapered bore, for example, a bore having a larger inner diameter at a downstream end and a smaller inner diameter at an upstream end. Other numbers, types, and/or arrangements of electrodes may be used in various embodiments.

The emitter focusing electrode 130 is disposed proximate to the emitter 120. In the illustrated embodiment, the emitter focusing electrode 130 is positioned such that at least a portion of the emitter focusing electrode 130 overlaps at least a portion of the emitter 120 in the downstream direction 104, with the portion of the emitter focusing electrode 130 that overlaps the emitter 120 disposed axially outward (with the electron beam 102 defining the axis) from the emitter 120 and surrounding the emitter 120 in the axial direction. In some embodiments, the emitter focusing electrode 130 may be disposed immediately downstream of the emitter 120 (e.g., not overlapping in the downstream direction, but either abutting or having a very small gap between the emitter 120 and the emitter focusing electrode 130 in the downstream direction 104). In some embodiments, the emitter focusing electrode is formed as a substantially continuous annular member (e.g., a ring). In some embodiments, the emitter focusing electrode may include a plurality of segments, with the emitter focusing electrode configured as a segment electrode as discussed elsewhere herein.

In some embodiments, one or more portions of the emitter focusing electrode 130 may be maintained at a voltage potential that is less than a voltage potential of the emitter 120. The potential difference between the emitter 120 and the emitter focusing electrode 130 inhibits the movement of electrons generated from the emitter 120 from moving towards the emitter focusing electrode 130. For example, the emitter focusing electrode 130 may be maintained at a negative potential with respect to that of the emitter 120, with the negative potential with respect to the emitter 120 acting to focus the electron beam 102 away from the emitter focusing electrode 130, thereby facilitating focusing the electron beam 102 towards the target 116.

In some embodiments, one or more portions of the emitter focusing electrode 130 may be maintained at a voltage potential that is equal to or substantially similar to the voltage potential of the emitter 120. The similar voltage potential of the emitter focusing electrode 130 with respect to the voltage potential of the emitter 120 helps generate a substantially parallel electron beam by shaping electrostatic fields due the shape of the emitter focusing electrode 130. The emitter focusing electrode 130 may be maintained at a voltage potential that is equal to or substantially similar to the voltage potential of the emitter 120 via use of a lead (not shown in FIG. 5) that couples the emitter 120 and the emitter focusing electrode. Additionally or alternatively, the voltage potential of the emitter focusing electrode 130 may be adjustable between a potential substantially similar to the potential of the emitter 120 and a negative potential with respect to the potential of the emitter 120.

The electrode assembly 128 of the injector 110 further includes an extraction electrode 140 disposed proximate to and downstream of the emitter focusing electrode 130. The extraction electrode 140 is also disposed downstream of the emitter 120 and upstream with respect to the target 116, and is configured to additionally shape, control, and/or focus the electron beam 102. In some embodiments, the extraction electrode 140 may be formed as a generally continuous ring shaped member disposed axially outwardly of the emitter 120 and the electron beam 102. In alternate embodiments, other shapes may be employed for the extraction electrode 140 (e.g., elliptical, polygonal, or the like). The extraction electrode may include a plurality of segments, with the extraction electrode configured as a segment electrode as discussed elsewhere herein.

In some embodiments, one or more portions of the extraction electrode 140 may be negatively biased with respect to the emitter 120. For example, a bias voltage power supply 142 may supply a voltage to the extraction electrode 140 such that the extraction electrode 140 is maintained at a negative bias voltage with respect to the emitter 120. In some embodiments, the negative bias voltage may be variable. For example, the negative bias voltage may be variable between a maximum amplitude of negative bias voltage and a minimum amplitude of negative bias voltage. The minimum amplitude of negative bias voltage, in some embodiments, may be about zero volts of bias with respect to the voltage of the emitter 120. The bias voltage of the extraction electrode 140 may be adjusted via a control electronics module 144, which may control the bias voltage responsive to an operator input from, for example, an operator console.

Further, in some embodiments, one or more portions of the extraction electrode 140 may also be selectably positively biased with respect to the emitter 120. For example, the bias voltage power supply 142 may supply a voltage to the extraction electrode 140 such that the extraction electrode 140 is maintained at a positive bias voltage with respect to the emitter 120. The electrode assembly 128 may be configured so that an operator may selectably switch between a positive bias voltage and a negative bias voltage for the extraction electrode 140. For example, a number of pre-set voltages may be selectable between a maximum negative bias voltage and a maximum positive voltage bias, or, as another example, the bias voltage may be substantially continuously adjustable between the maximum negative bias voltage and the maximum positive voltage bias (e.g., via use of a dial, slider, or the like on a control panel or operator console).

The electrode assembly 128 of the injector 110 further includes a downstream focusing electrode 150 disposed proximate to and downstream of the extraction electrode 140. In the illustrated embodiment, one downstream focusing electrode 150 is shown. In some embodiments, additional downstream focusing electrodes may be employed. The downstream focusing electrode 150 is thus also disposed downstream of the emitter 120 and upstream with respect to the target 116, and is configured to additionally shape, control, and/or focus the electron beam 102. In the illustrated embodiment, the downstream focusing electrode 150 is formed as generally continuous ring shaped member disposed axially outwardly of the emitter 120 and the electron beam 102. In alternate embodiments, other shapes may be employed for the downstream focusing electrode 150 (e.g., elliptical, polygonal, or the like). In some embodiments, the downstream focusing electrode may include a plurality of segments, with the downstream focusing electrode configured as a segment electrode as discussed elsewhere herein.

One or more portions of the downstream focusing electrode 150 may be positively biased with respect to the emitter 120. It should be noted that in some embodiments the downstream focusing electrode 150 may additionally be configured to aid in extraction of the electron beam and thus may also be understood as or referred to as a downstream extraction electrode. For example, a bias voltage power supply 152 may supply a voltage to the downstream focusing electrode 150 such that the extraction electrode 140 is maintained at a positive bias voltage with respect to the emitter 120. In some embodiments, the positive bias voltage may be variable. For example, the positive bias voltage may be variable between a maximum amplitude of positive bias voltage and a minimum amplitude of positive bias voltage. The bias voltage of the downstream focusing electrode 150 may be adjusted via a control electronics module 154, which may control the bias voltage responsive to an operator input from, for example, an operator console. For example, a number of pre-set voltages may be selectable between the maximum positive bias voltage and the minimum positive voltage bias, or, as another example, the bias voltage may be substantially continuously adjustable between the maximum positive bias voltage and the minimum positive voltage bias (e.g., via use of a dial, slider, or the like on a control panel or operator console).

It may be noted that, in an X-ray tube, energy of an X-ray beam may be controlled via one or more of a plurality of techniques. For example, the energy of an X-ray beam may be controlled by altering the potential difference (e.g., acceleration voltage) between the cathode (e.g., emitter) and the anode (e.g., target), or by filtering the electron beam. This may be generally referred to as "kV control." The intensity of an X-ray beam may also be controlled via control of the electron beam current. (As used herein, the term "electron beam current" refers to the flow of electrons per second between the cathode and the anode.) Such a technique of controlling the intensity may be generally referred to as "mA control." As discussed herein, aspects of some embodiments provide for control an electron beam current via one or more electrodes, such as the extraction electrode 140 and/or the downstream focusing electrode 150. It may be noted that the use of such electrodes may enable a decoupling of the control of electron emission from the acceleration voltage or potential difference between the emitter 120 and the target 116.

In some embodiments, the extraction electrode 140 and/or the downstream focusing electrode 150 are configured for microsecond current control. For example, the electron beam current may be controlled on the order of microseconds by altering the voltage applied to one or more of the extraction electrode 140 or the downstream focusing electrode 150 on the order of microseconds. It may be noted the emitter 120 may be treated as an infinite source of electrons. In accordance with aspects of some embodiments, electron beam current, which is typically a flow of electrons from the emitter 120 toward the target 116, may be controlled by altering the voltage potential of one or more of the extraction electrode 140 or the downstream focusing electrode 150. In some embodiments, the size (e.g., width, diameter, cross-sectional area) of an electron beam may be controlled via control of the bias voltage of one or more of the extraction electrode 140 or the downstream focusing electrode 150. Further, in some embodiments, the intensity of the electron beam may also be controlled via control of the bias voltage of one or more of the extraction electrode 140 or the downstream focusing electrode 150.

In some embodiments, the emitter focusing electrode 130 may be maintained at substantially the same voltage as the emitter 120, while the extraction electrode 140 may be biased at a negative voltage with respect to the emitter 120 and the emitter focusing electrode 130. By way of example, the voltage potential of the emitter 120 (as well as the emitter focusing electrode 130) may be about −140 kV, the voltage of the extraction electrode may be maintained at less than the about −140 kV of the emitter 120, and the downstream focusing electrode 150 may be maintained at about −135 kV or higher to positively bias the downstream focusing electrode 150 with respect to the emitter 120 (as well as the extraction electrode 140). In some embodiments, an electric field 170 is generated between the downstream focusing electrode 150 and the extraction electrode 140 due to the potential difference between the downstream focusing electrode 150 and the extraction electrode 140. The strength of the electric field 170 thus generated may be used to control the intensity of an electron beam generated by the emitter 120 towards the target 116. The intensity of the electron beam 102, for example, may therefore be controlled by controlling the strength of the electric field 170. For instance, the electric field 170 causes the electrons emitted from the emitter 120 to be accelerated towards the target 116. The stronger the electric field 170, the stronger is the acceleration of the electrons from the emitter 120 towards the target 116. Similarly, the weaker the electric field 170, the lesser is the acceleration of electrons from the emitter 120 towards the target 116. Further, a differential between the bias voltage of the extraction electrode 140 and the bias voltage of the downstream focusing electrode 150 may be defined and altered by altering one or more of the bias voltage of the extraction electrode 140 and the bias voltage of the downstream focusing electrode 150. The intensity of the electron beam may be increased as the differential increases, therefore providing for control of intensity of the electron beam by adjusting the voltage differential.

Furthermore, in some embodiments, voltage shifts (e.g., of about 8 kV or less) may be applied to one or more of the extraction electrode 140 or the downstream focusing electrode 150 (or portions thereof) to control the intensity of the electron beam 102. In some embodiments, these voltage shifts may be applied to the extraction electrode 140 via use of the control electronics module 144 and the downstream focusing electrode 150 via use of the control electronics module 154. The voltage applied to one or more of the extraction electrode 140 or the downstream focusing electrode 150 may be changed in intervals from about 1-15 microseconds to intervals of about at least 150 milliseconds. In some embodiments, the control electronics modules 144, 154 may include Si switching technology circuitry to change the voltage applied to one or more of the extraction electrode 140 or the downstream focusing electrode 150. In some embodiments, where the voltage shifts may range beyond 8 kV, a silicon carbide (SiC) switching technology may be applied. Changes in voltage applied to one or more of the extraction electrode 140 or the downstream focusing electrode 150 thus may facilitate changes in intensity of the electron beam 102 in intervals of about 1-15 microseconds, for example. The control of the intensity of the electron beam on the order of microseconds may be referred to as microsecond intensity switching.

The X-ray tube assembly 100 depicted in FIG. 5 also includes a magnetic assembly 160 for focusing and/or positioning and deflecting the electron beam 102 on the target 116. In some embodiments, the magnetic assembly 160 may be disposed between the injector 110 and the target 116 (e.g. downstream of the extraction electrode 140, downstream of the downstream focusing electrode 150, and upstream of the target 116). In the illustrated embodiment, the magnetic assembly 160 includes magnets 162 for influencing focusing of the electron beam 102 by creating a magnetic field that shapes the electron beam 102 on the target 116. The magnets 162 may include or more quadrupole magnets, on or more dipole magnets, or combinations thereof. As the properties of the electron beam current and voltage may change rapidly, the effect of space charge and electrostatic focusing in the injector 110 will change accordingly. To help maintain a stable focal spot size, or quickly modify focal spot size according to system requirements, the magnetic assembly 160 provides a magnetic field having a performance controllable from steady-state to a sub-30 microsecond time scale for a wide range of focal spot sizes. In some embodiments, the magnetic assembly 160 may be configured to provide a magnetic field having a performance controllable from steady-state to a sub-10 microsecond time scale. This helps provide protection of the X-ray source system, as well as achieving CT system performance requirements.

Further, in some embodiments, the magnetic assembly 160 may include one or more dipole magnets for deflection and positioning of the electron beam 102 at a desired location on the X-ray target 116. The electron beam 102 that has been focused and positioned impinges upon the target 116 to generate the X-rays 180. The X-rays 180 generated by collision of the electron beam 102 with the target 116 may be directed from the X-ray tube 180 through an opening in the tube casing 118, which may be generally referred to as an X-ray window 164, towards an object (not shown in FIG. 5.)

The electrons in the electron beam 102 may get backscattered after striking the target 116. Therefore, the X-ray tube assembly 100 may include an electron collector 166 for collecting electrons that are backscattered from the target 116. In some embodiments, the electron collector 166 may be maintained at a ground potential. In some embodiments, the electron collector 166 may be maintained at a potential that is substantially similar to the potential of the target 116. The electron collector 166 may be located proximate to the target 116 to collect the electrons backscattered from the target 116. For example, in some embodiments, the electron collector 166 may be located between the emitter 120 and the target 116 (e.g. downstream of the emitter 120 and upstream of the target 116), and, in some embodiments, the electron collector 166 may be disposed closer to the target 116 than to the extraction electrode 140. The electron collector 166 may be formed from a refractory material, such as, but not limited to, molybdenum. As another example, the electron collector 166 may be formed from copper. In still another embodiment, the electron collector 166 may be formed from a combination of a refractory metal and copper.

In some embodiments, the X-Ray tube assembly 100 may include a positive ion collector (not shown) to attract positive ions that may be produced due to collision of electrons in the electron beam 102 with the target 116. The positive ion collector is generally placed along the electron beam path and prevents the positive ions from striking various components in the X-ray tube assembly 100.

Figure 6:
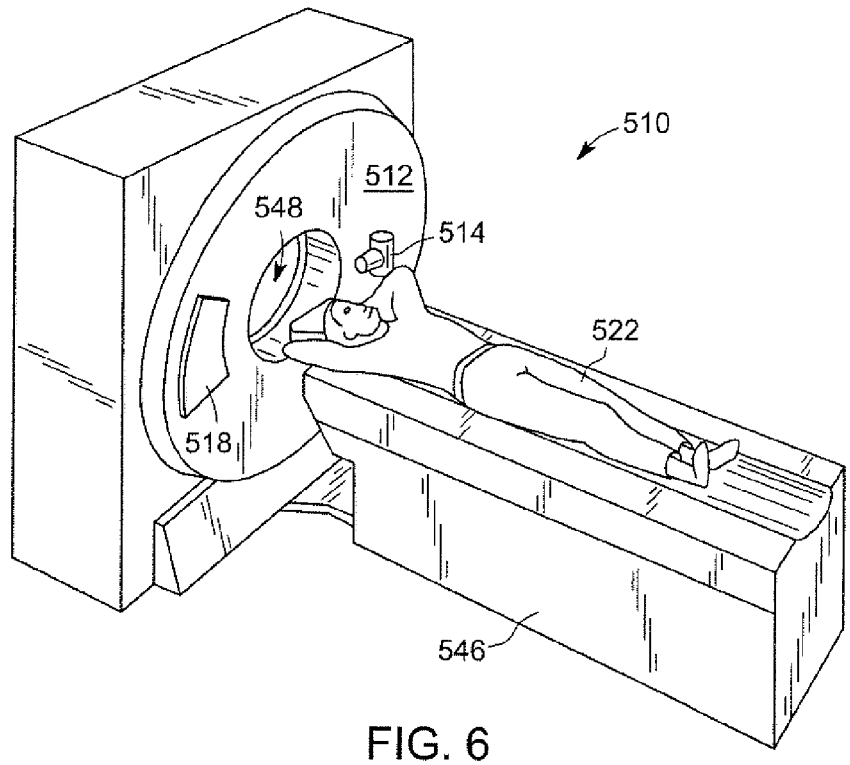
FIG. 6 is a pictorial view of a computed tomography (CT) imaging system in accordance with various embodiments.
Figure 7:
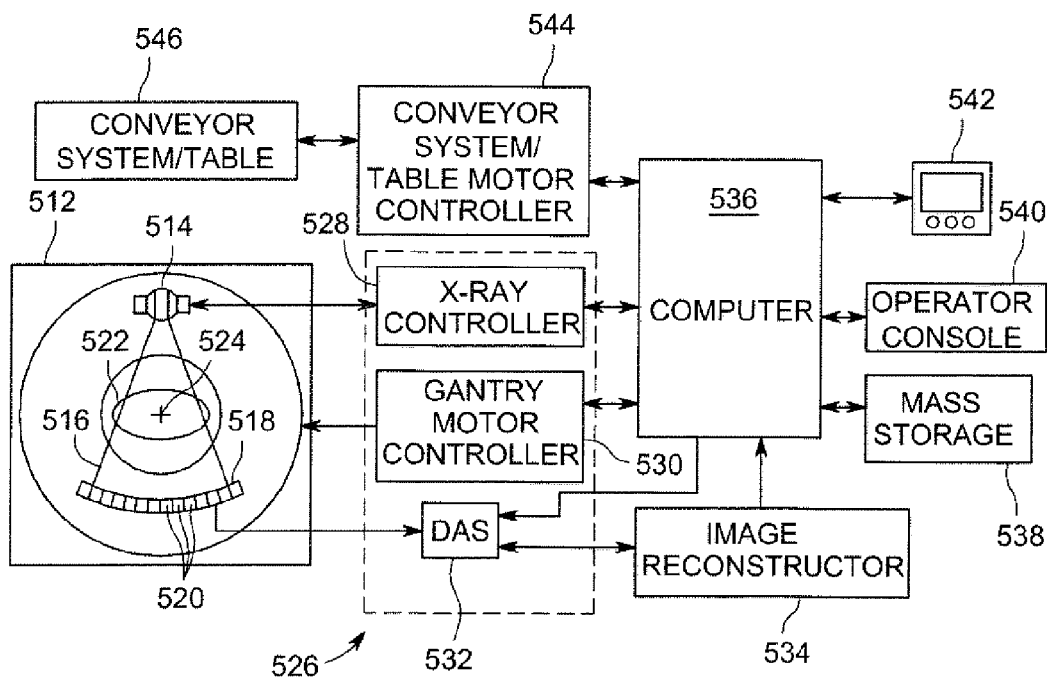
FIG. 7 is a block schematic diagram of the CT imaging system of FIG. 6 in accordance with various embodiments.

An X-ray assembly, such as the X-ray tube assembly 100, formed in accordance with various embodiments, may be used in conjunction with a computed tomography (CT) system. FIG. 6 provides a pictorial view of a computed tomography (CT) imaging system 510 in accordance with an embodiment, and FIG. 7 provides a block schematic diagram of the CT imaging system 510 of FIG. 6 in accordance with various embodiments. The CT imaging system 510 includes a gantry 512. The gantry 512 has an X-ray source 514 configured to project a beam of X-rays 516 toward a detector array 518 positioned opposite the X-ray source 514 on the gantry 512. The X-ray source 514 may include an X-ray tube assembly such as the X-ray tube assembly 100. In some embodiments, the gantry 512 may have multiple X-ray sources (e.g., along a patient theta or patient Z axis) that project beams of X-rays. The detector array 518 is formed by a plurality of detectors 520 which together sense the projected X-rays that pass through an object to be imaged, such as a medical patient 522. During a scan to acquire X-ray projection data, the gantry 512 and the components mounted thereon rotate about a center of rotation 524. While the CT imaging system 510 is described in connection with FIG. 6 with reference to the medical patient 522, it should be noted that the CT imaging system 510 may have applications outside of the medical realm. For example, the CT imaging system 510 may be utilized for ascertaining the contents of closed articles, such as luggage, packages, etc., and in search of contraband such as explosives and/or biohazardous materials.

Rotation of the gantry 512 and the operation of the X-ray source 514 are governed by a control mechanism 526 of the CT system 510. The control mechanism 526 includes an X-ray controller 528 that provides power and timing signals to the X-ray source 514 and a gantry motor controller 530 that controls the rotational speed and position of the gantry 512. A data acquisition system (DAS) 532 in the control mechanism 526 samples analog data from the detectors 520 and converts the data to digital signals for subsequent processing. An image reconstructor 534 receives sampled and digitized X-ray data from the DAS 532 and performs high-speed reconstruction. The reconstructed image is applied as an input to a computer 536, which stores the image in a mass storage device 538.

Moreover, the computer 536 may also receive commands and scanning parameters from an operator via operator console 540 that may have an input device such as a keyboard (not shown in FIGS. 6 and 7). An associated display 542 allows the operator to observe the reconstructed image and other data form the computer 536. Commands and parameters supplied by the operator are used by the computer 536 to provide control and signal information to the DAS 532, the X-ray controller 528, and the gantry motor controller 530. Additionally, the computer 536 may operate a table motor controller 544, which controls a motorized table 546 to position the patient 522 and/or the gantry 512. For example, the table 546 may move portions of the patient 522 through a gantry opening 548. It may be noted that in certain embodiments, the computer 536 may operate a conveyor system controller 544, which controls a conveyor system 546 to position an object, such as baggage or luggage, and the gantry 512. For example, the conveyor system 546 may move the object through the gantry opening 548.

In some embodiments, the operator console 540 may be configured to allow an operator to vary or adjust a beam profile intensity of an electron beam and/or an X-ray beam. For example, a controller (e.g., the X-ray controller 528) may, responsive to an operator input, vary the bias voltage of one or more segments of a segmented electrode to vary or adjust a beam intensity profile. The operator may be provided with predetermined settings corresponding to particular voltages, and/or an operator may substantially continuously adjust one or more settings using a dial, slider, keypad, touchscreen, or the like. In some embodiments, an operator may enter a particular procedure or application at the operator console 540, and voltage settings for the electrode segments may be automatically selected by a processor of the CT imaging system 510 to provide an appropriate beam intensity profile for the particular procedure or application. As another example, the operator may input, for example, a bias voltage for one or more electrode segments and/or a desired beam intensity profile.

Figure 8:
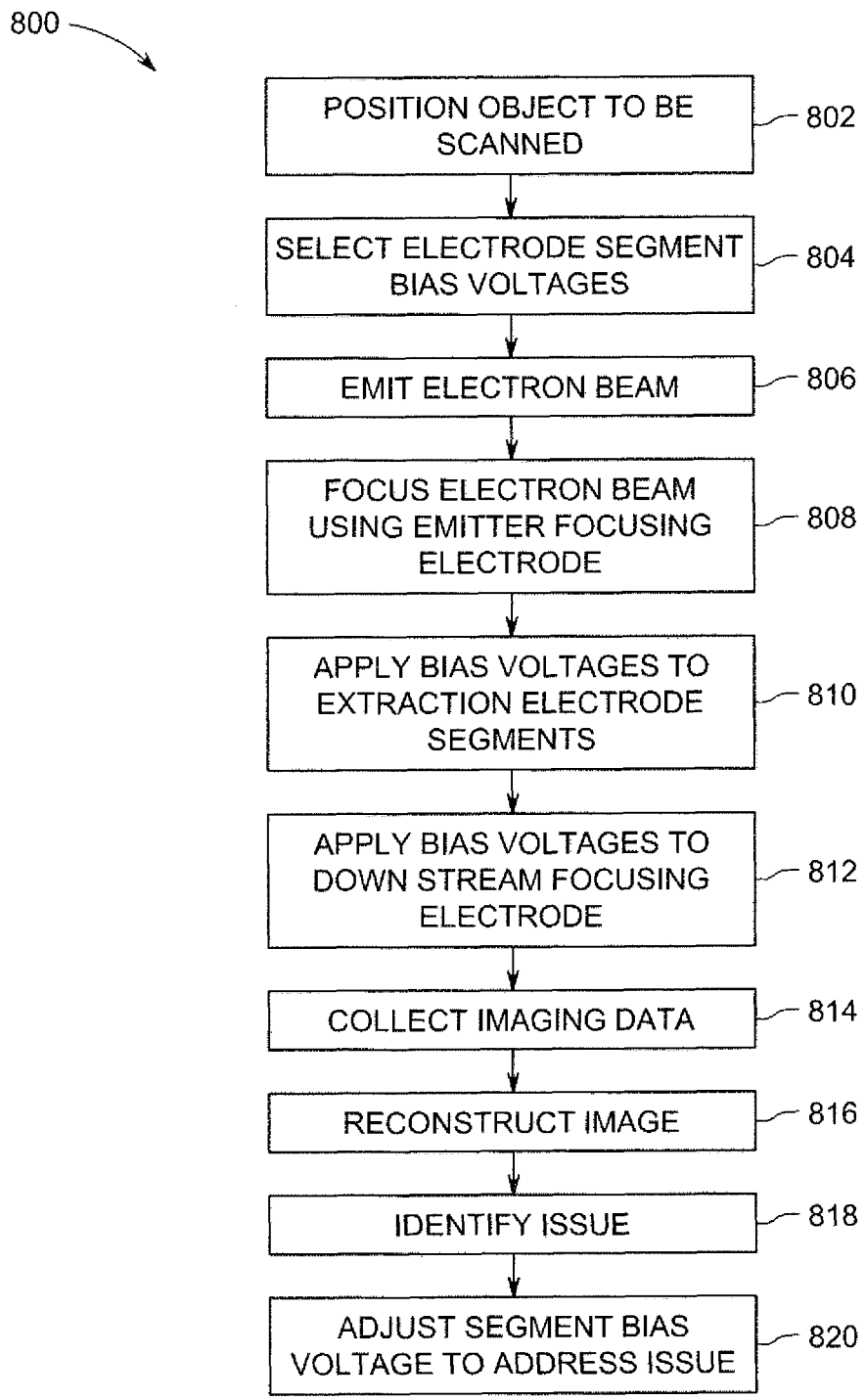
FIG. 8 is a flowchart of an exemplary method for performing an X-ray scan in accordance with various embodiments.

FIG. 8 is a flow chart of a method 800 for performing a X-ray scan in accordance with an embodiment. The method 800, for example, may employ structures or aspects of various embodiments discussed above. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion.

At 802, an object to be scanned is positioned. For example, in some embodiments, the object may be a patient placed on a bed or table that is advanced through a gantry for performing a CT scan. As another example, in some embodiments the object may be a piece of luggage or a package that is placed on a conveyor belt and advanced to a scanning location.

At 804, bias voltages for segments of a segmented electrode are selected. In some embodiments, one or more of an extraction electrode, a downstream focusing electrode, or an emitter focusing electrode may be configured as a segmented electrode. For example, in various embodiments, the extraction electrode may be segmented while the emitter focusing electrode and downstream focusing electrode may not be; the emitter focusing electrode may be segmented while the extraction electrode and downstream focusing electrode may not be; or the downstream focusing electrode may be segmented while the extraction electrode and the emitter focusing electrode may not be. In some embodiments, one or more electrode segment bias voltages may be selected directly or indirectly by an operator via an input entered at an operator console. For example, an operator may indirectly select one or more bias voltages by specifying a desired electron beam intensity profile or characteristic of such a profile, a desired X-ray beam intensity profile or characteristic of such a profile, or a particular procedure or application for which a processing unit is configured to select appropriate electrode segment bias voltages. In some embodiments, an operator console may present predetermined settings to an operator (e.g., via prompts provided on a touchscreen or otherwise). As another example, in some embodiments, an operator may directly enter one or more electrode segment bias voltages. Additionally or alternatively, one or more electrode segment bias voltages may be adjustable substantially continuously. In some embodiments, the bias voltage of the extraction electrode (or one or more segments thereof) may be set to a negative bias voltage relative to the emitter voltage, and the bias voltage of the downstream focusing electrode (or one or more segments thereof) may be set to a positive bias voltage relative to the emitter voltage.

At 806, an electron beam is emitted from an emitter (e.g., emitter 120). For example, an emitter (from which electrons are emitted) may be maintained at a negative voltage with respect to a target (toward which electrons are directed). For example, the target may be maintained at a positive voltage (e.g., about 140 kV) and the emitter maintained at about 0 V. As another example, the target may be maintained at about 0 V, and the emitter maintained at about −140 kV. As yet another example, the target may be maintained at a positive voltage, the emitter maintained at a negative voltage, and a frame to which the target and emitter are attached may be grounded. The emitter may be heated directly or indirectly. As the electron beam proceeds downstream from the emitter toward the target, the electron beam proceeds through the extraction electrode and the downstream focusing electrode.

At 808, the electron beam is focused using an emitter focusing electrode (e.g., emitter focusing electrode 130). The emitter focusing electrode may be, for example, a substantially continuous ring-shaped member disposed proximate to and at least partially surrounding (in an axial direction) the emitter. In some embodiments, the emitter focusing electrode is maintained at substantially the same voltage as the emitter, which may result in an electron beam having substantially parallel edges. In some embodiments, the emitter focusing electrode may be maintained at a negative bias voltage with respect to the emitter. In some embodiments, the emitter focusing electrode may be a segmented electrode having a plurality of segments, with one or more segment having a bias voltage that differs from one or more other segments, with one or more of the various segment bias voltages selected at 804.

At 810, one or more bias voltages is applied to the electrode segments of an extraction electrode. For example, the bias voltage may have been selected at 804. The extraction electrode may be a substantially ring-shaped member centered about the electron beam emitted from the emitter. In some embodiments, the extraction electrode is disposed proximate to the emitter focusing electrode, and is disposed downstream of the emitter focusing electrode. The extraction electrode may be disposed by a relatively small gap downstream of the emitter focusing electrode. In the depicted embodiment, the extraction electrode is a segmented electrode having a plurality of segments, with one or more segment having a bias voltage that differs from one or more other segments, with one or more of the various segment bias voltages selected at 804. The extraction electrode segment voltages, in various embodiments, may be positive, negative, or a combination thereof.

At 812, a positive bias voltage is applied to the downstream focusing electrode. The downstream focusing electrode may be a substantially ring-shaped member centered about the electron beam emitted from the emitter. In some embodiments, the downstream focusing electrode is disposed proximately to the extraction electrode, and is disposed downstream of the extraction electrode. The downstream focusing electrode may be disposed by a relatively small gap downstream of the extraction electrode. In some embodiments, the combination of a selected negative bias voltage for the extraction electrode and a positive bias voltage for the downstream focusing electrode results in the inhibition or suppression of the emission of electrons from a portion of the emitter, resulting in a reduced emission area and a smaller size (e.g., width, diameter, and/or cross-sectional area of an electron beam). In some embodiments, the downstream focusing electrode may be a segmented electrode having a plurality of segments, with one or more segment having a bias voltage that differs from one or more other segments, with one or more of the various segment bias voltages selected at 804.

At 814, imaging data is collected during the performance of the scan. For example, a gantry including an X-ray source and associated components may rotate about an object being scanned, while a detector array (e.g., detector array 518) senses the projected X-rays that pass through the object. In other embodiments, imaging data may be collected while an object, such as a package or luggage is advanced by a scanning area on a conveyor belt, carrousel, or other device. In still other embodiments, a scanning device and object being scanned may remain substantially stationary with respect to each other during a scan.

At 816, an image is reconstructed using the imaging data collected at 814. In some embodiments, an image reconstructor (e.g., image reconstructor 534) may receive sampled and digitized X-ray data and perform a high-speed reconstruction.

At 818, an issue to be addressed by a modification of beam intensity profile is identified. The issue, for example, may be a heel effect that is having a negative impact on image quality. As another example, the issue may be an artifact. The issue may be identified by an operator, or, additionally or alternatively, the issue may be identified autonomously by a processing unit performing a diagnostic analysis on one or more of an electron beam, an X-ray beam, or an image. In some embodiments, an operator identifies an issue and a processing unit is configured to determine an adjustment to address the issue.

At 820, one or more electrode segment bias voltages are adjusted to address the issue identified in 818. In some embodiments, a first combination of electrode voltages may result in an image adversely affected by an artifact or heel effect. One or more voltages may then be changed to arrive at a second combination of electrode voltages, resulting in a modified beam intensity profile that eliminates, reduces, and/or minimizes the artifact or heel effect. For example, electrode segment bias voltages may be adjusted to provide a modified beam intensity profile to account for a detected or otherwise determined heel effect. The modification of the intensity profile may be done during a scan, for example, as an artifact is detected, or may be performed between scans. In some embodiments, one or more electrode segment bias voltages may be adjusted to provide a modified beam having a modified beam intensity profile to perform a scan corresponding to a new or different application or procedure of scan to be performed on a different object than the object that was previously imaged. As still another example, the scanning system may have a default setting, and the bias voltages of the electrode segments may be adjusted to return to the default setting after successful scanning and/or imaging of an object. Further still, adjustments may be made to one or more of the bias voltages to change a voltage differential between the extraction electrode and the downstream focusing electrode, whereby a field between the extraction electrode and downstream focusing electrode may be altered to adjust an intensity of the electron beam. Thus, in some embodiments, the intensity, the size, and the beam intensity profile distribution of the electron beam may be adjusted.

Thus, embodiments provide systems and methods wherein a beam intensity profile of a beam associated with an X-ray system may be adjusted. For example, a heel effect or artifact may be addressed by adjusting the beam intensity profile. Also, the beam intensity profile may be adjusted dynamically on-site during a scan or between scans. Thus, some embodiments provide for improved adjustability of electron and/or X-ray beam intensity profiles, and/or improved resolution, for example, for X-ray imaging.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer", "controller", and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:
1. An X-ray tube assembly comprising:
an emitter configured to emit an electron beam defining a downstream direction toward a target, the emitter disposed proximate an upstream end of the X-ray tube assembly;
an electrode assembly disposed proximate the emitter and downstream of the emitter, the electrode assembly comprising at least one electrode having a bias voltage with respect to the emitter, the electrode assembly configured to surround the electron beam in an axial direction, wherein the electrode assembly comprises:

an emitter focusing electrode disposed proximate the emitter and outward of the emitter in the axial direction, at least a portion of the emitter focusing electrode overlapping at least a portion of the emitter in the downstream direction;

an extraction electrode disposed proximate the emitter focusing electrode, the extraction electrode disposed downstream of the emitter and the emitter focusing electrode; and a downstream focusing electrode disposed proximate the extraction electrode and downstream of the extraction electrode, the downstream focusing electrode configured to surround the electron beam in the axial direction, the downstream focusing electrode having a positive bias voltage with respect to the emitter; and at least one electrode of the electrode assembly being a segmented electrode, the segmented electrode comprising a plurality of segments arranged about an axis defined by the electron beam, the plurality of segments including a first member and a second member, the first member configured to have a first bias voltage and the second member configured to have a second bias voltage that is different from the first bias voltage.

2. The assembly in accordance with claim 1, wherein the first member and the second member are configured to have independently adjustable bias voltages, the assembly further comprising a control module operably connected to the electrode assembly, the control module configured to control a first bias voltage of the first member and a second bias voltage of the second member, wherein a first beam intensity profile is produced by a first combination of the first bias voltage and the second bias voltage, and wherein a different, second beam intensity profile is produced by a different, second combination of the first bias voltage and the second bias voltage.

3. The assembly in accordance with claim 2, wherein the segmented electrode comprises an opposed pair comprising the first member and the second member, the first member symmetrically opposed to the second member about the axis defined by the electron beam, the first member and the second member defining an opposed pair axis passing substantially through the center of the first member and the second member, wherein adjusting a voltage bias of the first member relative to a voltage bias of the second member alters a beam intensity profile along the opposed pair axis.

4. The assembly in accordance with claim 3, wherein the segmented electrode comprises a plurality of opposed pairs, the plurality of opposed pairs defining a substantially continuous geometric shape disposed about the axis defined by the electron beam and defining a plane substantially perpendicular to the electron beam.

5. The assembly in accordance with claim 4, wherein the segmented electrode defines a ring surrounding the axis defined by the electron beam, the segmented electrode comprising four segments, each segment comprising a substantially circular arcuate segment corresponding to a quadrant of the ring.

6. The assembly in accordance with claim 1, wherein the extraction electrode is configured as the segmented electrode.

7. The assembly in accordance with claim 6, wherein the extraction electrode has a negative bias voltage setting wherein at least one segment of the extraction electrode has a negative bias voltage with respect to the emitter at the negative bias voltage setting.

8. The assembly in accordance with claim 1, wherein the downstream focusing electrode is configured as the segmented electrode.

9. An X-ray tube assembly comprising:

an emitter configured to emit an electron beam defining a downstream direction, the emitter disposed proximate an upstream end of the X-ray tube assembly;

a target disposed proximate a downstream end of the X-ray tube assembly and configured to receive the electron beam emitted from the emitter, the target configured to provide an X-ray beam responsive to a collision of the electron beam with the target;

an electrode assembly disposed proximate the emitter and downstream of the emitter, the electrode assembly comprising at least one electrode having a bias voltage with respect to the emitter, the electrode assembly configured to surround the electron beam in an axial direction, wherein the electrode assembly comprises:

an emitter focusing electrode disposed proximate the emitter and outward of the emitter in the axial direction, at least a portion of the emitter focusing electrode overlapping at least a portion of the emitter in the downstream direction;

an extraction electrode disposed proximate the emitter focusing electrode, the extraction electrode disposed downstream of the emitter and the emitter focusing electrode; and a downstream focusing electrode disposed proximate the extraction electrode and downstream of the extraction electrode, the downstream focusing electrode configured to surround the electron beam in the axial direction, the downstream focusing electrode having a positive bias voltage with respect to the emitter;

at least one electrode of the electrode assembly being a segmented electrode, the segmented electrode comprising a plurality of segments arranged about an axis defined by the electron beam and substantially surrounding the axis, the plurality of segments including a first member and a second member, the first member and the second member configured to have independently adjustable bias voltages;

a control module operably connected to the electrode assembly, the control module configured to control a first bias voltage of the first member and a second bias voltage of the second member, wherein a first beam intensity profile is produced by a first combination of the first bias voltage and the second bias voltage, and wherein a different, second beam intensity profile is produced by a different, second combination of the first bias voltage and the second bias voltage, the control module configured to adjust the first bias voltage and the second bias voltage to address at least one of an identified artifact or change in procedure; and a focusing magnet assembly disposed downstream of the electrode assembly and upstream of the target, the focusing magnet assembly configured to deflect or position the electron beam on the target.

10. The assembly in accordance with claim 9, wherein the segmented electrode comprises an opposed pair comprising the first member and the second member, the first member symmetrically opposed to the second member about the axis defined by the electron beam, the first member and the second member defining an opposed pair axis passing substantially through the center of the first member and the second member, wherein adjusting a voltage bias of the first member relative to a voltage bias of the second member alters a beam intensity profile along the opposed pair axis.

11. The assembly in accordance with claim 10, wherein the segmented electrode comprises a plurality of opposed pairs, the plurality of opposed pairs defining a substantially continuous geometric shape disposed about the axis defined by the electron beam and defining a plane substantially perpendicular to the electron beam.

12. The assembly in accordance with claim 11, wherein the segmented electrode defines a ring surrounding the axis defined by the electron beam, the segmented electrode comprising four segments, each segment comprising a substantially circular arcuate segment corresponding to a quadrant of the ring.

13. The assembly in accordance with claim 9, wherein the extraction electrode is configured as the segmented electrode.

14. The assembly in accordance with claim 13, wherein the extraction electrode has a negative bias voltage setting wherein at least one segment of the extraction electrode has a negative bias voltage with respect to the emitter at the negative bias voltage setting.

15. The assembly in accordance with claim 9, wherein the downstream focusing electrode is configured as the segmented electrode.

16. The assembly in accordance with claim 9, further comprising an electron collector disposed downstream of the emitter and upstream of the target.

17. A method for providing an electron beam, the method comprising:
emitting an electron beam toward a target, the electron beam defining a downstream direction from the emitter toward the target;
focusing the electron beam using an electrode assembly having at least one electrode having a bias voltage with respect to the emitter, the electrode assembly having at least one segmented electrode, the segmented electrode comprising a plurality of segments arranged about an axis defined by the electron beam, the plurality of segments including a first member and a second member, the first member and the second member configured to have independently adjustable bias voltages;
identifying an artifact;
adjusting, to address the artifact via a control module, at least one of a first bias voltage of the first member or a second bias voltage of the second member from a first combination of bias voltages to a different, second combination of bias voltages, wherein a first beam intensity profile is produced by the first combination of the bias voltages, and wherein a different, second beam intensity profile is produced by the second combination of the bias voltages, and
wherein the electrode assembly comprises an emitter focusing electrode disposed proximate the emitter, at least a portion of the emitter focusing electrode overlapping at least a portion of the emitter in the downstream direction, an extraction electrode disposed proximate the emitter focusing electrode, the extraction electrode configured as the segmented electrode and disposed downstream of the emitter and the emitter focusing electrode, and a downstream focusing electrode disposed proximate the extraction electrode and downstream of the extraction electrode, the method further comprising providing a negative bias voltage to at least one segment of the extraction electrode.

18. The method in accordance with claim 17, further comprising:
identifying an artifact in an image corresponding to information acquired using the first beam intensity profile; and
selecting an adjustment to the beam intensity profile to address the artifact.

19. The method in accordance with claim 17, wherein the segmented electrode comprises an opposed pair comprising the first member and the second member, the first member symmetrically opposed to the second member about the axis defined by the electron beam, the first member and the second member defining an opposed pair axis passing substantially through the center of the first member and the second member, the method further comprising adjusting a voltage bias of the first member relative to a voltage bias of the second member to alter a beam intensity profile along the opposed pair axis.

20. The method in accordance with claim 19, wherein the segmented electrode comprises a plurality of opposed pairs defining a plurality of opposed pair axes, the method further comprising adjusting bias voltages of members of a plurality of the plurality of opposed pairs to alter the beam intensity profile along a plurality of the plurality of opposed pair axes.

* * * * *